United States Patent
Fromage

(10) Patent No.: US 9,808,655 B2
(45) Date of Patent: Nov. 7, 2017

(54) METHOD FOR DETERMINING PARTIAL PRESSURE OF A GASEOUS CONSTITUENT AND REGULATOR OF BREATHING MASK FOR AIRCRAFT OCCUPANT

(75) Inventor: Matthieu Fromage, Saint-Arnoult-en-Yvelines (FR)

(73) Assignee: Zodiac Aerotechnics, Plaisir (FR)

( * ) Notice: Subject to any disclaimer, the term of this patent is extended or adjusted under 35 U.S.C. 154(b) by 388 days.

(21) Appl. No.: 13/580,404

(22) PCT Filed: Feb. 28, 2011

(86) PCT No.: PCT/IB2011/000781
§ 371 (c)(1),
(2), (4) Date: Aug. 22, 2012

(87) PCT Pub. No.: WO2011/104635
PCT Pub. Date: Sep. 1, 2011

(65) Prior Publication Data
US 2012/0325207 A1     Dec. 27, 2012

Related U.S. Application Data

(60) Provisional application No. 61/308,476, filed on Feb. 26, 2010.

(51) Int. Cl.
*A62B 18/02* (2006.01)
*A62B 7/00* (2006.01)
(Continued)

(52) U.S. Cl.
CPC ............... *A62B 7/02* (2013.01); *A61M 16/00* (2013.01); *A62B 7/14* (2013.01); *A62B 9/00* (2013.01);
(Continued)

(58) Field of Classification Search
CPC .......... G01N 33/0073; G01N 33/0062; G01N 33/004; G01N 33/0026; G01N 33/0009; G01N 33/497
(Continued)

(56) References Cited

U.S. PATENT DOCUMENTS 3,395,701 A   8/1968   Bartlett et al.
3,907,657 A   9/1975   Heijne et al.
(Continued)

FOREIGN PATENT DOCUMENTS

WO       2012114145 A1     8/2012

OTHER PUBLICATIONS

International Search Report dated Jul. 29, 2011 in Application No. PCT/IB2011/000781.

*Primary Examiner* — Justine Yu
*Assistant Examiner* — Tu Vo
(74) *Attorney, Agent, or Firm* — Kilpatrick Townsend & Stockton LLP; Dean W. Russell; Kristin M. Crall

(57) ABSTRACT

A method for determining a characteristic such as partial pressure or percentage of a gaseous constituent in a first gas mixture flow in a flow chamber in which there is alternating flow in opposite directions between the first gas mixture flow and a second gas mixture flow. The steps may include a) introducing the first gas mixture flow into a sensing chamber when the first gas mixture flow flows in the flow chamber, b) preventing introduction of gas from the flow chamber into the sensing chamber at least when the second gas mixture flow flows in the flow chamber, c) sensing the characteristic of the first gas mixture flow in the sensing chamber.

13 Claims, 6 Drawing Sheets

(51) Int. Cl.
*A62B 7/02* (2006.01)
*A62B 7/14* (2006.01)
*A62B 18/00* (2006.01)
*A62B 9/00* (2006.01)
*A61M 16/00* (2006.01)
*A62B 9/02* (2006.01)
*B64D 10/00* (2006.01)

(52) U.S. Cl.
CPC .............. *A62B 9/006* (2013.01); *A62B 9/027* (2013.01); *A62B 18/00* (2013.01); *A62B 18/02* (2013.01); *B64D 10/00* (2013.01); *B64D 2231/025* (2013.01)

(58) Field of Classification Search
USPC ............ 128/202.11, 203.14, 203.25, 204.21, 128/204.26, 205.25, 206.21, 203.22, 128/200.24, 201.23, 201.28, 203.12, 128/203.16, 203.24, 203.29, 204.18, 128/203.21, 204.22, 203.26, 204.29, 128/205.11, 205.24; 73/23.3, 31.04
See application file for complete search history.

(56) References Cited

U.S. PATENT DOCUMENTS

| | | | |
|---|---|---|---|
| 4,272,329 A | | 6/1981 | Hetrick et al. |
| 4,272,331 A | | 6/1981 | Hetrick |
| 4,336,590 A | * | 6/1982 | Jacq et al. ............... 128/204.21 |
| 4,384,935 A | * | 5/1983 | De Jong ...................... 204/406 |
| 4,873,970 A | * | 10/1989 | Freidank ............. A62B 18/088 128/202.22 |
| 5,049,254 A | * | 9/1991 | Logothetis .......... F02D 41/0072 204/425 |
| 5,686,654 A | * | 11/1997 | Friese et al. ................. 73/23.32 |
| 6,789,539 B2 | | 9/2004 | Martinez |
| 7,040,319 B1 | | 5/2006 | Kelly et al. |
| 7,153,412 B2 | * | 12/2006 | Inaba et al. ................. 205/784.5 |
| 7,814,907 B2 | * | 10/2010 | Bremner et al. ......... 128/205.23 |
| 2009/0013996 A1 | | 1/2009 | Rittner et al. |
| 2009/0101149 A1 | * | 4/2009 | Bachelard et al. ...... 128/204.29 |
| 2009/0301489 A1 | * | 12/2009 | Bloch et al. ............. 128/204.23 |

* cited by examiner

METHOD FOR DETERMINING PARTIAL PRESSURE OF A GASEOUS CONSTITUENT AND REGULATOR OF BREATHING MASK FOR AIRCRAFT OCCUPANT

CROSS-REFERENCE TO RELATED APPLICATIONS

This application is the United States national phase of International Application No. PCT/IB2011/000781 filed on Feb. 28, 2011 and published in English on Sep. 1, 2011 as International Publication No. WO2011/104635, which application claims priority to U.S. Provisional Application No. 61/308,476 filed on Feb. 26, 2010, the contents of both of which are incorporated herein by reference.

FIELD OF THE INVENTION

The present invention relates to a method for determining a characteristic such as partial pressure or percentage of a gaseous constituent and a regulator of breathing mask for aircraft occupant. The gaseous constituent is in particular oxygen or carbon dioxide.

BACKGROUND OF THE INVENTION

The partial pressure or percentage of oxygen (and carbon dioxide) are particularly useful in order to satisfy the needs of the user while reducing the consumption in pure oxygen (provided by an oxygen cylinder, a chemical generator or a liquid oxygen converter) or gas highly enriched in oxygen provided in particular by an on-board oxygen generator system (OBOGS).

But, when two gases having different mixtures successively flow in opposite directions in a chamber, the measurement of a characteristic of a gaseous constituent in the first gas mixture flow is disturbed by the second gas mixture. The invention aims at reducing this problem.

SUMMARY OF THE INVENTION

For this purpose the invention provides a method for determining a characteristic such as partial pressure or percentage of a gaseous constituent in a first gas mixture flow in a flow chamber where flows alternatively said first gas mixture flow and a second gas mixture flow in opposite directions comprising the following steps:

a) introducing the first gas mixture flow into a sensing chamber when the first gas mixture flow flows in the flow chamber, b) preventing introduction of gas from the flow chamber into the sensing chamber at least when the second gas mixture flow flows in the flow chamber, c) sensing said characteristic of the first gas mixture flow in the sensing chamber.

According to another feature in accordance with the invention, preferably the method further has the following steps:

providing a user with a breathing mask for aircraft occupant including a demand regulator, generating a respiratory gas flow by breathing in of the user into the flow chamber, and generating an exhalation gas flow by breathing out of the user into the flow chamber, one amongst the respiratory gas flow and the exhalation gas flow being the first gas mixture flow and the other being the second gas mixture flow.

According to a supplementary feature in accordance with the invention, preferably the method further has the following steps:

splitting the flow chamber in a respiratory chamber and sensing chamber, inserting an isolation valve between the sensing chamber and the respiratory chamber, in order to prevent introduction of the second gas mixture flow into the sensing chamber, generating the first gas mixture flow into the respiratory chamber, by breathing of the user into the respiratory chamber.

According to a supplementary feature in accordance with the invention, preferably the method further comprising feeding the respiratory chamber with the first gas mixture flow through the sensing chamber and the isolation valve.

According to an alternative feature in accordance with the invention, preferably the method comprising feeding sensing chamber with the first gas mixture flow through the respiratory chamber and the isolation valve.

According to another feature in accordance with the invention, preferably the method further comprises introducing the first gas mixture flow into the sensing chamber from the flow chamber during step a).

According to a supplementary feature in accordance with the invention, preferably the method further comprises:

d) detecting the occurrence of the first gas mixture flow in the flow chamber, during step a), putting the sensing chamber in flow communication with the flow chamber when the occurrence of the first gas mixture flow in the flow chamber is detected.

According to another supplementary feature in accordance with the invention, preferably the method further comprises preventing communication between the flow chamber and the sensing chamber when the occurrence of the first gas mixture flow in the flow chamber is not detected.

According to another feature in accordance with the invention, preferably the method further comprises:

placing a solid ionic conductor of a pump electrochemical cell interposed between the flow chamber and the sensing chamber, and during step a), pumping said gas constituent from the flow chamber into the sensing chamber through the solid ionic conductor.

Otherwise, the invention provides a method for protecting aircraft occupant comprising the steps of:

a) providing a user with a breathing mask for aircraft occupant, b) providing a respiratory gas including a mixture of breathable gas and dilution gas to the user, c) sensing partial pressure or percentage of oxygen or carbon dioxide in exhalation gas flow generated by the user, d) adjusting the rate of oxygen or breathable gas in the respiratory flow in accordance with the partial pressure or percentage of oxygen or carbon dioxide.

It appears that the partial pressure or percentage of oxygen or carbon dioxide in exhalation gas flow is an efficient indication concerning the oxygen need of user. Therefore, the consumption in oxygen can be accurately adjusted.

The invention also provides a breathing mask for aircraft occupant including a demand regulator, said regulator comprising:

a breathable gas supply line to be connected to a source of breathable gas and supplying a flow chamber with breathable gas, a dilution gas supply line to be connected to a source of dilution gas and supplying the flow chamber with dilution gas, a dilution adjusting device adjusting the rate of dilution gas in the respiratory gas supplied to the flow chamber, the dilution adjusting device comprising a dilution valve and a control device controlling the dilution valve in accordance with a dilution signal generated by the gas sensor in function of the partial pressure or percentage of oxygen or carbon dioxide in exhalation gas.

In advantageous embodiments, the breathing assembly preferably further has one or more of the following features:

BRIEF DESCRIPTION OF THE DRAWINGS

Other features and advantages of the present invention will appear in the following detailed description, with reference to the appended drawings in which.

DETAILED DESCRIPTION OF THE INVENTION

Figure 1:
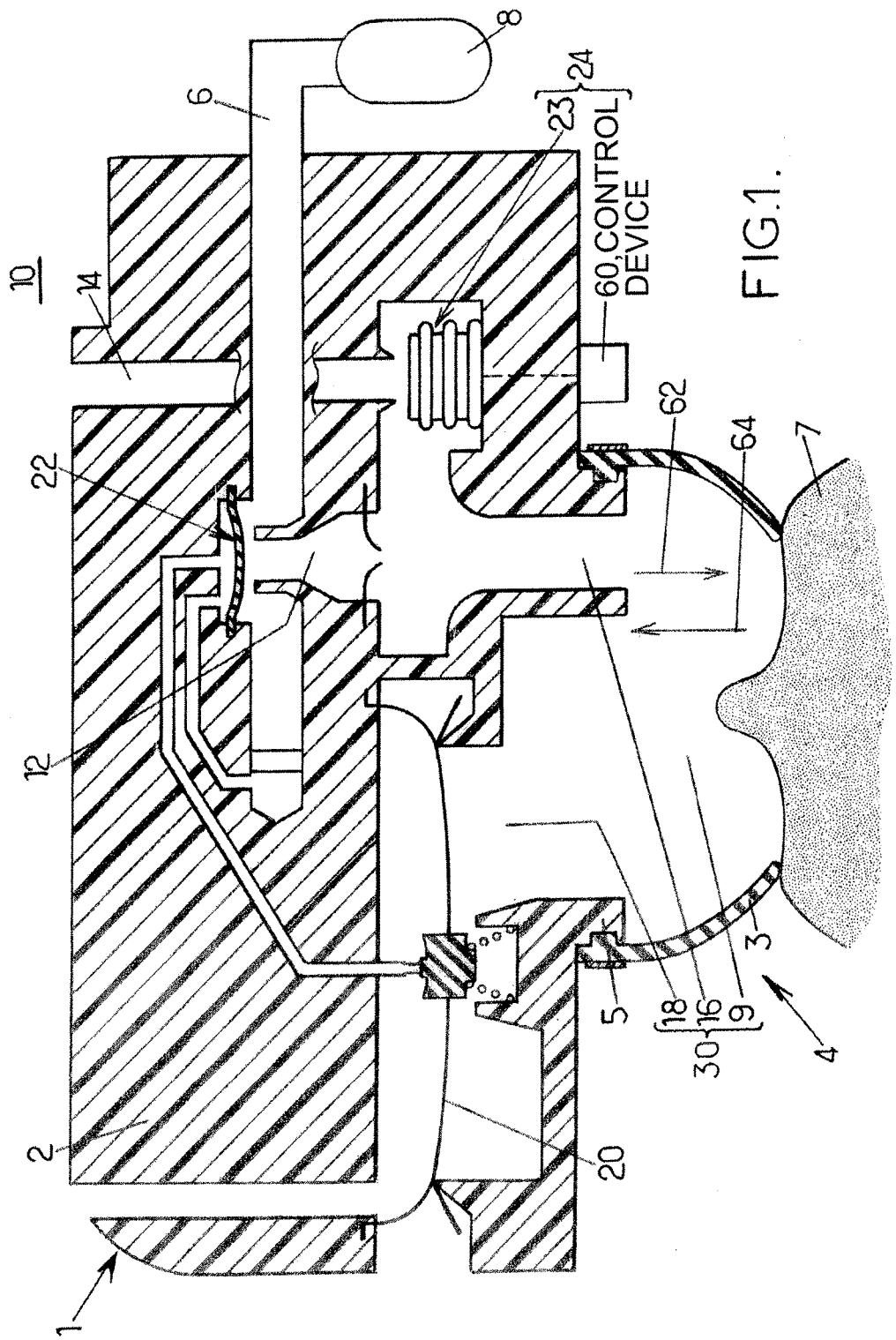
FIG. 1 shows a breathing mask comprising a flow chamber.

FIG. 1 discloses main functions of a breathing mask 4 for occupant of an aircraft, in particular for pilot disposed in a cabin 10 of an aircraft.

The breathing mask 4 comprises a demand regulator 1 and an oronasal face piece 3 fixed to a tubular connecting portion 5 of the regulator 1. When a user 7 dons the breathing mask 4, the oronasal face piece 3 is put to the skin of the user face 7 and delimits a respiratory chamber 9.

The demand regulator 1 has a casing 2 including a breathable gas supply line 12, a dilution gas supply line 14 and a respiratory gas supply line 16. The respiratory gas supply line 16 has a downstream end in fluid communication with the respiratory chamber 9.

The breathable gas supply line 12 is supplied at its upstream end with pressurized oxygen by a source of breathable gas 8 through a feeding duct 6. In the embodiment shown, the pressurized source of breathable gas 8 is a cylinder containing pressurized oxygen. The breathable gas supply line 12 supplies the respiratory chamber 9 with breathable gas through the respiratory gas supply line 16, the downstream end of the breathable gas supply line 12 being directly in fluid communication with the upstream end of the respiratory gas supply line 16.

The dilution gas supply line 14 is in communication by its upstream end with a source of dilution gas. In the illustrated embodiment, the dilution gas is air and the source of dilution gas is the cabin 10 of the aircraft. The dilution gas supply line 14 supplies the respiratory chamber 9 with dilution gas through the respiratory gas supply line 16, the downstream end of the dilution gas supply line 14 being directly in fluid communication with the upstream end of the respiratory gas supply line 16. So, in the embodiment illustrated, the breathable gas and the dilution gas are mixed in the respiratory gas supply line 16 of the casing 2, i.e. before supplying the respiratory chamber 9 through the tubular connecting portion 5. Therefore a flow 62 of respiratory gas flows in the respiratory gas supply line 16 and the respiratory chamber 9, the respiratory gas including breathable gas and dilution gas mixed.

The regulator 1 further comprises an exhaust line 18 and an exhaust valve 20. The exhaust valve 20 is disposed between the downstream end of the exhaust line 18 and the cabin 10 (ambient air). The upstream end of the exhaust line 18 is in communication with the respiratory chamber 9 of the oronasal face piece 3 through the tubular connecting portion 5 and receives a flow 64 of gas exhaled by the user. Concerning the exhaust of the exhalation gas flow 64, the exhaust valve 20 functions as a check valve which opens under the pressure of the exhalation gas flow 64 and closes for preventing air of the cabin 10 from entering into the flow chamber 30.

The user 7 breathes in and breathes out in the respiratory chamber 9. The exhalation line 18 is in communication directly or through the respiratory chamber 9 with the respiratory gas supply line 16. Therefore, the gas supply line 16, the respiratory chamber 9 and the exhalation line 18 define a flow chamber 30 without separation.

The demand regulator 1 further has a pressure adjusting device 22 and a dilution adjusting device 24.

The pressure adjusting device 22 adjusts the pressure in the flow chamber 30 and in particular in the respiratory chamber 9. In the embodiment illustrated, the pressure adjusting device 22 comprises in particular a main valve disposed between the feeding duct 6 and the respiratory gas supply line 16.

The dilution adjusting device 24 adjusts the rate of oxygen in the respiratory gas flow 62. In the embodiment illustrated, the dilution adjusting device comprises in particular a dilution valve 23 and a control device. The dilution valve 23 is disposed between the dilution gas supply line 14 and the respiratory gas supply line 16. The control device controls the dilution valve 23.

Demand regulator starts supplying first gas mixture (respiratory gas) in response to the user of the breathing mask breathing in and stops supplying respiratory gas when the user stops breathing in.

One can refers to prior art, such as for example to document U.S. Pat. No. 6,789,539 for a more detailed description of a demand regulator. The present invention is also applicable to other types of dilution adjusting device 24, such as the dilution adjusting device disclosed in patent application PCT/FR2011/050359 or U.S. Pat. No. 6,789,539 included by reference.

Figure 2:
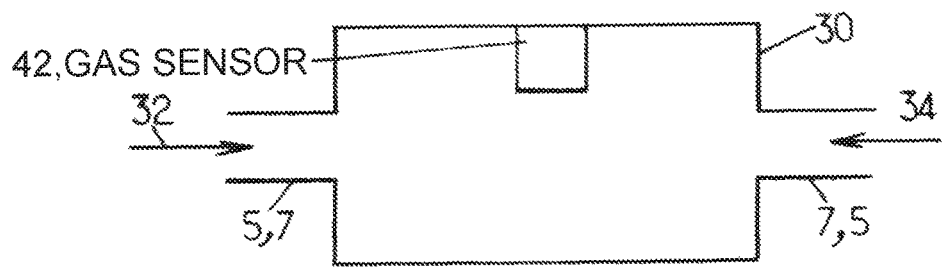
FIG. 2 schematically represents a first flow and a second flow in the flow chamber of the breathing mask, according to a sensing device not within the scope of the invention.

FIG. 2 schematically represents the flow chamber 30 in which alternatively flows a first gas mixture flow 32 and a second gas mixture flow 34. In order to adjust the rate of oxygen to deliver to the user 7, a characteristic (in particular the partial pressure or percentage of a gaseous) of a gaseous constituent (in particular oxygen or carbon dioxide) of the first gas mixture flow 32 is to be detected by a gas sensor.

The first gas mixture flow 32 may be either the respiratory gas flow 62 or the exhalation gas flow 64, which means that the characteristic of the gaseous constituent to sense may be either in the respiratory gas or in the exhalation gas. So, the first gas mixture flow 32 flows from the tubular connecting portion 5 to (the mouth or nose of) the user 7 or from the user 7 to the tubular connecting portion 5. Conversely, the second gas mixture flow 34 may be either the exhalation gas flow 64 or the respiratory gas flow 62.

Figure 3:
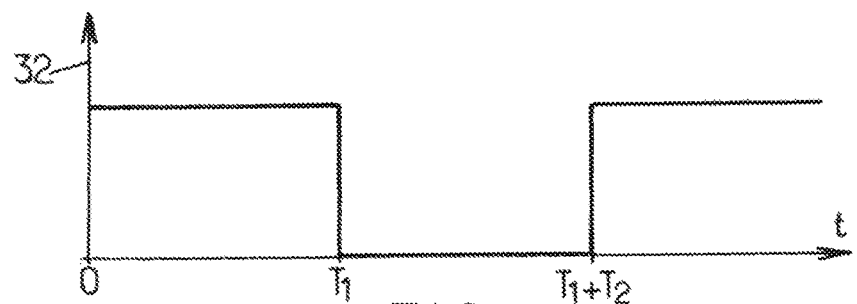
FIG. 3 represents variations of the first flow in the flow chamber during the time.

As represented schematically in FIG. 3, between the time 0 and the time $T_1$, the gas content in the flow chamber 30 reaches the gas content of the first gas mixture flow 32 and then between the time $T_1$ and the time $T_1+T_2$, the first gas mixture flow 32 becomes absent from the flow chamber 30.

Figure 4:
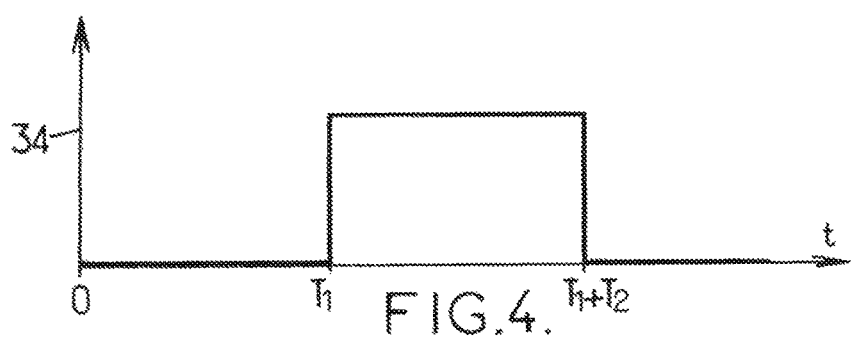
FIG. 4 represents variations of the second flow in the flow chamber during the time.

As represented schematically in FIG. 4, between the time 0 and the time $T_1$, the second gas mixture flow 34 becomes absent from the flow chamber 30 and then, between the time $T_1$ and the time $T_1+T_2$, the gas content in the flow chamber 30 reaches the gas content of the second gas mixture flow 34.

It should be noticed that in FIGS. 3 and 4 the time for filing the flow chamber 30 is neglected.

So, it may be considered by simplification that successively during a $T_1$ period the first gas mixture flow 32 flows in the flow chamber 30 in a first direction, then during a $T_2$ period the second gas mixture flow 34 flows into the flow chamber 30 in a second direction opposite to the first direction, then the first gas mixture flow 32 flows again in the flow chamber 30 during another $T_1$ period, and so on. The $T_1$ period may be considered as equal to the $T_2$ period, and called T.

The gaseous content of the first gas mixture flow 32 being different from the second gas mixture flow 34, the second gas mixture flow 34 disturbs the measurement of the characteristic of the gaseous content of the first gas mixture flow 32. It should be understood that the first gas mixture and the second gas mixture may content the same constituents (at least some identical constituents), and only differ in the percentage of some of the constituents (in particular percentage of oxygen, carbon dioxide and steam).

Figure 5:
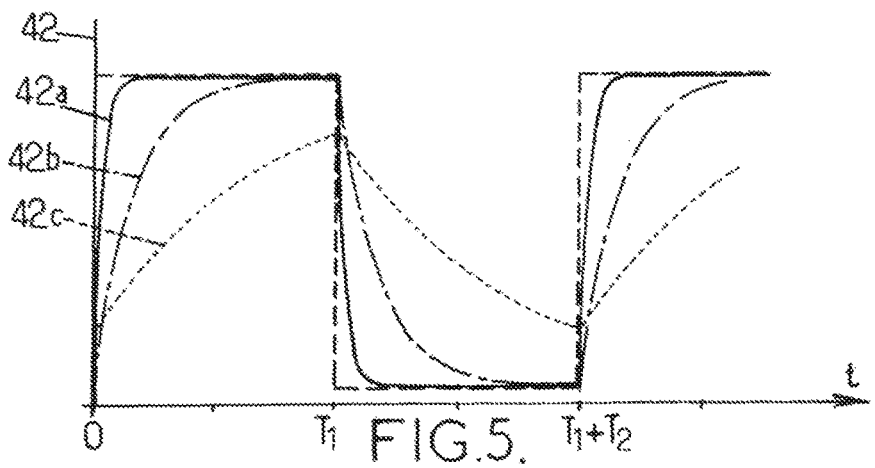
FIG. 5 represents measurements provided by gas sensors placed in the flow chamber.

FIG. 5 presents three measurements 42a, 42b, 42c provided by gas sensors having different response times Tr for the above described example. The measurements 42a, 42b, 42c correspond to gas sensors having a response time respectively equal to T/10, T/2 and 2T.

It appears that the gas sensor providing measurements 42a, 42b are suitable for the present example, whereas the gas sensor providing measurement 42c is not appropriate.

So, the shorter the response time of the gas sensor is, the more accurate the measurement is. But, a sensor with a short time response is generally more expensive than a sensor with a longer time response, and sometimes a sensor with a time response satisfying for a particular application does not exist.

Figure 6:
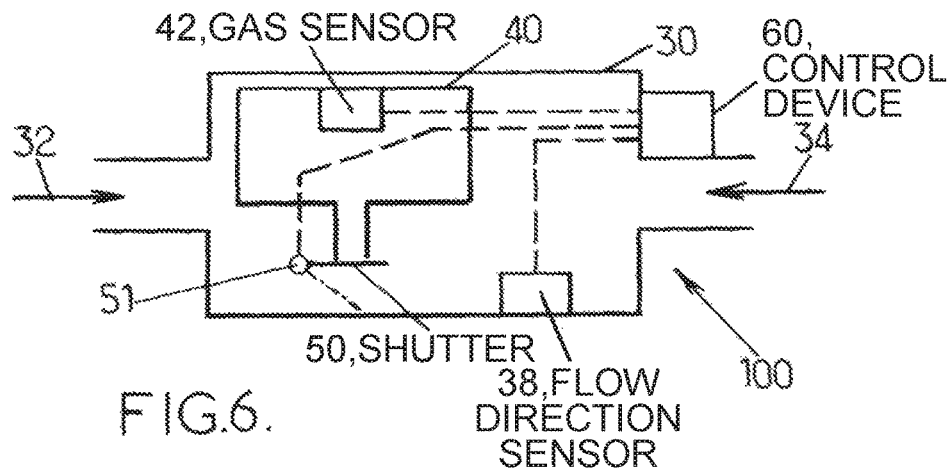
FIG. 6 represents a first embodiment of a sensing device in accordance with the invention.

FIG. 6 represents a first embodiment of a device 100 in accordance with the invention. The device 100 is a portion of the breathing mask 4 represented in FIG. 1.

The device 100 comprises a flow direction sensor, a shutter, a driving device 51 and a gas sensor placed in a sensing chamber 40 in fluid communication with the flow chamber 30 through a passage 66.

The flow direction sensor and the gas sensor are connected to the control device. The flow direction sensor detects if the flow direction in the flow chamber 30 corresponds to the direction of the first flow mixture 32. In variant, the flow direction sensor may detect if the flow direction in the flow chamber 30 corresponds to the direction of the second flow mixture 34.

The shutter movable between an active position in which it closes the passage 66 and an inactive position in which it is away from the passage 66.

The control device 60-controls the driving device 51 in order to place the shutter open position when the flow direction sensor detects the first gas flow 32, so that the first gas mixture flow 32 (partially) enters in the sensing chamber 40. Moreover, the control device controls the driving device 51 in order to place the shutter in closed position when the flow direction sensor does not detect the first gas flow 32, so that the second the second gas mixture flow 34 is prevented from entering in the sensing chamber 40.

Therefore, the sensing chamber 40 contains only gas mixture of the first gas mixture flow 32 at any time. So, the gas sensor transmits a dilution signal which accuracy is not influenced by the second gas mixture flow 34. The control device controls the dilution valve 24 in accordance with the dilution signal generated by the gas sensor.

The gas sensor is adapted to determine in particular partial pressure (or percentage) in oxygen (or carbon dioxide) of the gas contained in the sensing chamber 40.

The flow direction sensor includes in particular a pressure sensor, a pressure gauge sensor, a pressure differential sensor, thermistances, a sensor of the state of a check valve or a piezo sensor device comprising a flexible sheet and detecting the direction of the curvature of the flexible sheet.

Figure 7:
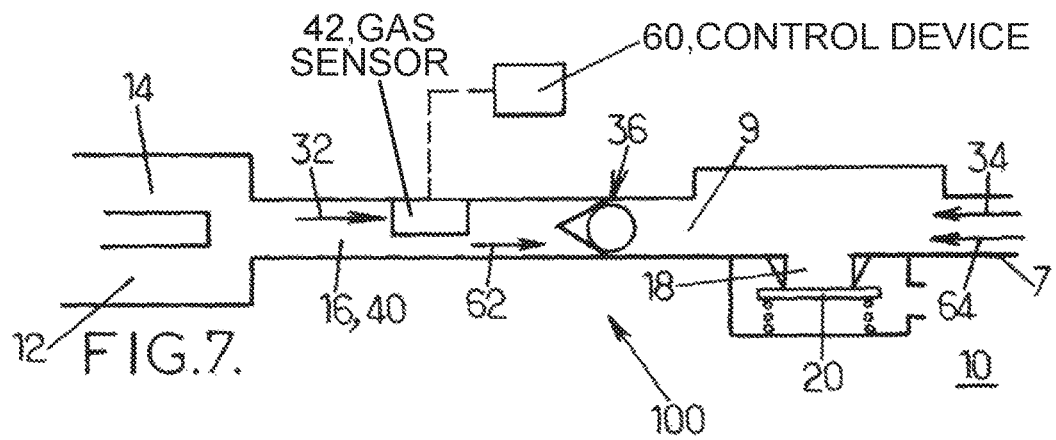
FIG. 7 represents a second embodiment of a sensing device in accordance with the invention.

FIG. 7 represents a second embodiment of a device 100 in accordance with the invention.

In this second embodiment, the characteristic of the gaseous constituent to sense is in the respiratory gas, so that the first gas mixture flow 32 is the respiratory gas flow 62 and the second gas mixture flow 34 is the exhalation gas flow 64.

An isolation valve 36 is inserted between the respiratory gas supply line 16 and the respiratory chamber 9. The gas sensor, in connection with the control device, is placed in the respiratory chamber 16 which forms the sensing chamber 40. The isolation valve 36 prevents gas from entering into the sensing chamber 16, 40 from the respiratory chamber 9.

In the embodiment illustrated, the isolation valve 36 is a check valve. In variant, it may be an inspiration valve similar to the exhaust valve 20.

Figure 8:
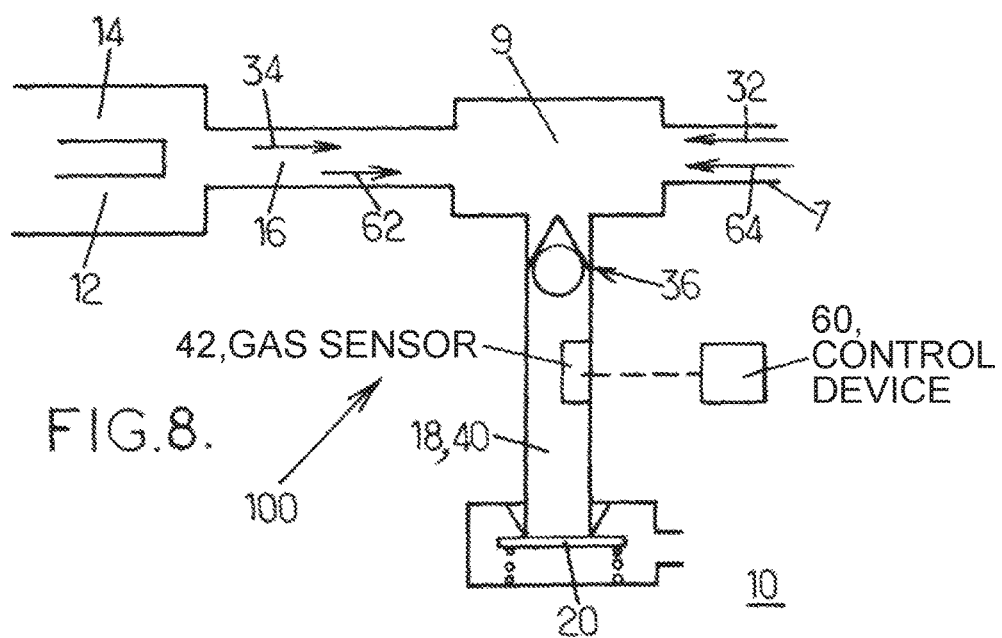
FIG. 8 represents a third embodiment of a sensing device in accordance with the invention.

FIG. 8 represents a third embodiment of a device 100 in accordance with the invention.

In this third embodiment, the characteristic of the gaseous constituent to sense is in the exhalation gas, so that the first gas mixture flow 32 is the exhalation gas flow 64 and the second gas mixture flow 34 is the respiratory gas flow 62.

The isolation valve 36 is inserted between the respiratory chamber 9 and the exhalation line 18. The gas sensor, in connection with the control device, is placed in the exhalation line 18 which forms the sensing chamber 40. The isolation valve 36 prevents gas from entering into the respiratory chamber 9 from the exhalation line 18.

Figure 9:
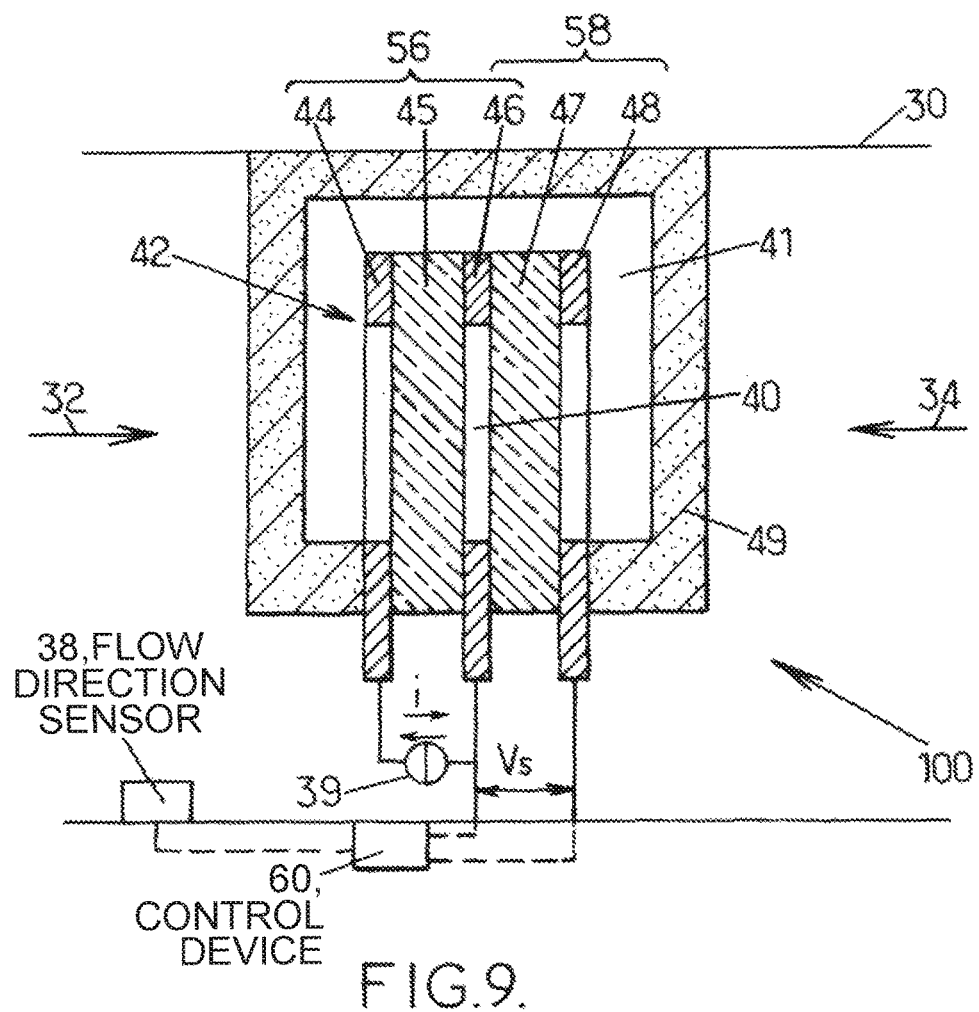
FIG. 9 represents a fourth embodiment of a sensing device in accordance with the invention.

FIG. 9 represents a fourth embodiment of a device 100 in accordance with the invention.

The gas detector comprises a pumping plate 44, a first disk of solid ionic conductor 45, a common plate 46, a second disk of solid ionic conductor 47 and a sensing plate 48.

The pumping plate 44, the common plate 46 and the sensing plate 48 are electrodes preferably made of platinum films.

The pumping plate 44, the common plate 46 and the sensing plate 48 are of substantially annular form. Therefore, the sensing chamber 40 is delimited by the common plate 46, the first ionic conductor 45 and the second ionic conductor 47.

A current source 39 is inserted between the pumping plate 44 and the common plate 46. The common plate 46 and the sensing plate 48 are connected to the control device, as well as the flow direction sensor.

The pumping plate 44, the first solid ionic conductor 45 and the common plate 46 define a pumping electrochemical cell 56. The common plate 46, the second solid ionic conductor 47 and the sensing plate 48 define a sensing electrochemical cell 58.

The ionic conductors 45, 47 define solid electrolyte. They are preferably made in zirconium dioxide suitably adapted for the conduction of ions of oxygen $O_2$.

The gas sensor further comprises an optional filter 49 surrounding the pumping electrochemical cell 56 and the sensing electrochemical cell 58. The filter 49 prevents particles from entering into the sensor. Therefore, the gas sensor includes a buffer chamber 41 extending between the flow chamber 30 and the pumping electrochemical cell 56 (and the sensing electrochemical cell 58).

The gas sensor may be placed either in the respiratory chamber 9, in the respiratory gas supply line 16 or in the exhalation line 18, and of any of the first to third embodiment described above.

Figure 10:
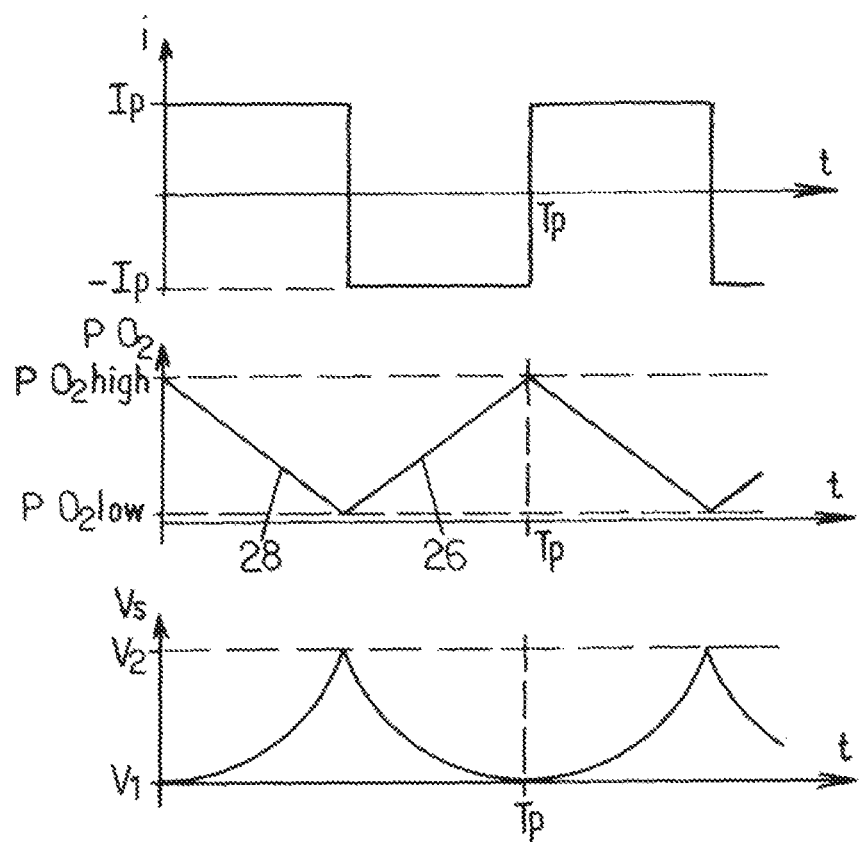
FIG. 10 represents a step of a method according to the invention using the sensing device of the fourth embodiment.

As illustrated in FIG. 10, when the electrical power supply 39 outputs a pumping current $\underline{i}$ at the value Ip, oxygen ions are transported through the ionic conductors 45 from the sensing chamber 40 to the buffer chamber 41. Therefore, an evacuation phase 28 corresponds to a phase of pumping current i equal to Ip. So, the partial pressure in Oxygen $PO_2$ in the sensing chamber 40 decreases. The voltage Vs between the sensing plate 48 and the common plate, called Nerst voltage, increases.

When the electrical power supply 39 outputs a pumping current $\underline{i}$ at the value $-$Ip, oxygen ions are transported through the ionic conductor 45 from the buffer chamber 41 to the sensing chamber 40. Therefore, a pressurisation phase 26 corresponds to a phase of pumping current i equal to $-$Ip. So, the partial pressure in Oxygen $PO_2$ in the sensing chamber 40 increases and the Nerst voltage Vs between the sensing plate 48 and the common plate 46 decreases.

In operation, the control device causes a repetitive sequence where the oxygen pumping current I is successively reversed to maintain the Nerst voltage Vs between to predetermined values $V_1$, $V_2$.

Therefore, the partial pressure of Oxygen in the sensing chamber 40 varies between two values $PO_2$low and $PO_2$high.

The period of oscillation Tp is proportional to the oxygen partial pressure in the buffer chamber 41. Therefore, period of the pumping cycle is used to determine the ambient oxygen partial pressure.

The transportation of the oxygen through the ionic conductor 45 during the pressurisation phase 26 creates a pressure drop in the buffer chamber 41. The low porosity of the external filter 49 limits the entry of the ambient gas into the sensor and is responsible of the main delay (high response time) in the oxygen partial pressure measurement.

The response time of the gas sensor generates an error in the measurement of the oxygen partial pressure in the first gas mixture flow 32, due to the second gas mixture flow 34.

Figure 11:
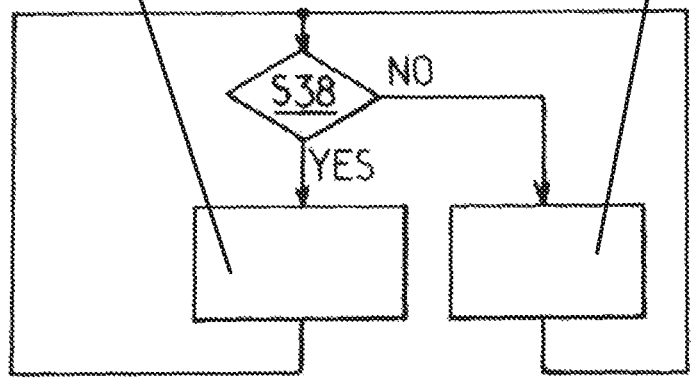
FIG. 11 is a flowchart representing different steps according to the invention.
Figure 12:
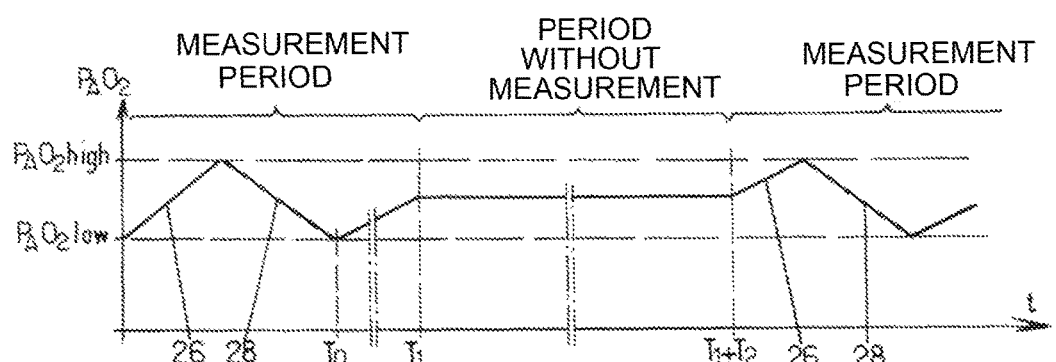
FIG. 12 represents a method according to the invention.

As shown in FIG. 11, in order to limit the error in the measurement of the oxygen partial pressure in the first gas mixture flow 32, the direction of the flow in the flow chamber 30 is sensed by the direction gas sensor. During step S38, based on the signal provided by the flow direction sensor, the control device determines if the flow in the flow chamber 30 is in the direction of the first gas mixture flow 32. If Yes, during a measurement period, the pressurization phase 26 and the evacuation phase 28 repetitively and alternatively follows one another. If No, as shown in FIG. 12, during a period without measurement, the pressurisation of the sensing chamber 40 is stopped, no pressurisation phase 26 occurring during the period without measurement. Consequently, diffusion of the second gas mixture flow 34 into the gas sensor buffer 41 is reduced and the sensing accuracy of the gas sensor 42 is improved. For example, the gas sensor measurement process is active during inspiration of the user and stopped during exhalation of the user if the characteristic of the gaseous component to be sensed is in the respiratory gas.

Figure 13:
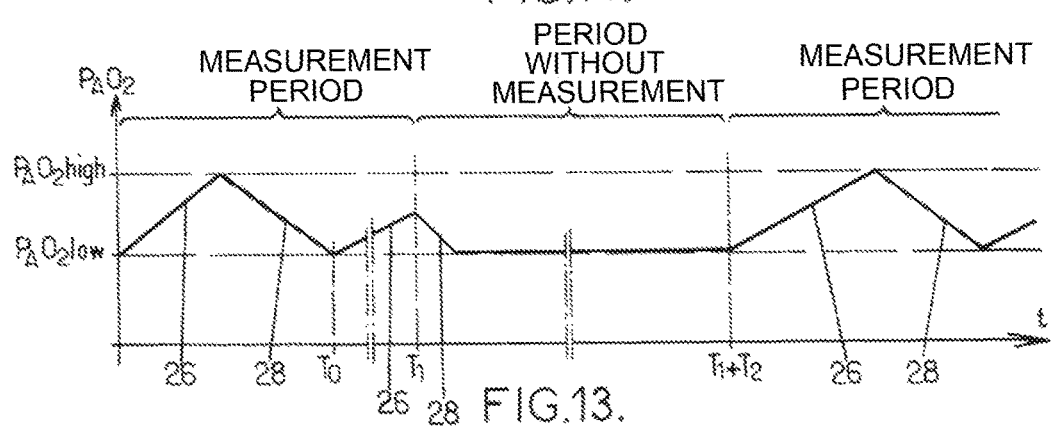
FIG. 13 represents a variation of the method represented in FIG. 12.

In a variant shown in FIG. 13, during the period without measurement, preferably at the beginning, an evacuation phase 28 is achieved. During the evacuation phase 28 of the period without measurement, as shown in FIG. 13, the pumping current i is preferably lower than during the evacuation phase 28 of the measurement period, i.e. lower than Ip. Therefore, the evacuation phase 28 of the period without measurement lasts during all the period without measurement or at least more than half of the period without measurement.

The invention claimed is:

1. A method for determining a partial pressure or percentage of a gaseous constituent in a first gas mixture flow in a flow chamber in which the first gas mixture flow flows alternatively in an opposite direction to a second gas mixture flow, the method comprising the steps of:
    a) providing a flow chamber comprising a gas sensor with a pump electrochemical cell, a sensing electrochemical cell and a sensing chamber, the pump electrochemical cell having a solid ionic conductor;
    b) detecting the first gas mixture flow in the flow chamber,
    c) pumping said gaseous constituent from the flow chamber into the sensing chamber through the solid ionic conductor of the pump electrochemical cell when the first gas mixture flow in the flow chamber is detected,
    d) stopping pumping said gaseous constituent from the flow chamber into the sensing chamber through the solid ionic conductor of the pump electrochemical cell when the first gas mixture flow is no longer detected in the flow chamber or when the second gas mixture flow flows in the flow chamber or both, and
    e) determining the partial pressure or percentage of gaseous constituent of the first gas mixture flow from data detected by the sensing electrochemical cell of the gas sensor.

2. The method according to claim 1 further comprising pumping said gaseous constituent from the sensing chamber back into the flow chamber through the solid ionic conductor when the second gas mixture flow flows in the flow chamber.

3. The method according to claim 2, wherein:
    the sensing electrochemical cell measures Nernst voltage, and wherein step e) further comprises measuring a period corresponding to variation of the Nernst voltage between two predetermined values during pumping of said gaseous constituent from the flow chamber into the sensing chamber or during pumping said gaseous constituent from the sensing chamber back into the flow chamber or both, and wherein the partial pressure or percentage of gaseous constituent of the first gas mixture flow is determined based on the measured period corresponding to variation of the Nernst voltage between the two predetermined values.

4. The method according to claim 1 wherein a buffer chamber is interposed between the flow chamber and the pump electrochemical cell, and the buffer chamber communicates with the flow chamber through a filter in low porous material.

5. The method according to claim 1, comprising sensing the partial pressure or percentage of oxygen in the first gas mixture flow.

6. The method according to claim 1, wherein steps b), c), d), and e) are repeated.

7. A method for regulating a rate of oxygen in respiratory gas provided by a breathing mask to an aircraft occupant, the method comprising the steps of:
 a) providing a breathing mask with a flow chamber comprising a gas sensor with a pump electrochemical cell, a sensing electrochemical cell and a sensing chamber, the pump electrochemical cell having a solid ionic conductor;
 b) generating a first gas mixture flow flowing into the flow chamber by mixing a pressurised breathable gas with a dilution gas,
 c) detecting presence of the first gas mixture flow in the flow chamber,
 d) pumping oxygen from the flow chamber into the sensing chamber through the solid ionic conductor of the pump electrochemical cell when the presence of the first gas mixture flow in the flow chamber is detected,
 e) stopping pumping oxygen from the flow chamber into the sensing chamber through the solid ionic conductor of the pump electrochemical cell when the first gas mixture flow in the flow chamber is no longer detected in order to prevent introduction of the second gas mixture flow from the flow chamber into the sensing chamber when the second gas mixture flow flows in the flow chamber,
 f) determining a partial pressure or percent of oxygen of the first gas mixture flow from sensing in the sensing chamber, and
 g) adjusting a delivery rate of the dilution gas to the respiratory gas.

8. The method according to claim 7, wherein steps b), c), d), and e) are repeated.

9. A sensing device for determining a partial pressure or percentage of oxygen, comprising:
 a flow chamber,
 a sensing chamber,
 a sensing electrochemical cell adapted to sense Nernst voltage which is a function of the oxygen in the sensing chamber,
 a selective device comprising:
  a solid ionic conductor of a pump electrochemical cell interposed between the flow chamber and the sensing chamber,
  electrical power adapted to alternatively pump oxygen from the flow chamber into the sensing chamber through the solid ionic conductor and from the sensing chamber into the flow chamber through the solid ionic conductor,
  a control device,
  a flow direction sensor connected to the control device and adapted to detect a first gas flow in a first direction and/or a second gas flow in a second direction opposite to the first direction, the control device controlling pumping said oxygen from the flow chamber into the sensing chamber through the solid ionic conductor of the pump electrochemical cell when the flow direction sensor detects presence of the first gas flow in the flow chamber and for stopping pumping oxygen from the flow chamber into the sensing chamber through the solid ionic conductor of the pump electrochemical cell when the flow direction sensor does not detect the first gas mixture flow in the flow chamber or when the presence of the first gas flow in the flow chamber is detected or both; and;
 a buffer chamber interposed between the flow chamber and the electrochemical cell, wherein the buffer chamber communicates with the flow chamber through a filter in low porous material.

10. A regulator of a breathing mask for an aircraft occupant, comprising the device according to claim 9 wherein the flow chamber is adapted to provide a respiratory gas to the aircraft occupant and the regulator further comprises:
 a breathable gas supply line to be connected to a source of breathable gas and supplying the flow chamber with breathable gas,
 a dilution gas supply line to be connected to a source of dilution gas and supplying the flow chamber with dilution gas,
 a dilution adjusting device for adjusting a delivery rate of dilution gas in the respiratory gas supplied to the flow chamber, the dilution adjusting device comprising a dilution valve, and the control device controlling the dilution valve in accordance with a dilution signal generated by the sensing electrochemical cell in function of the partial pressure or percentage of oxygen.

11. The regulator according to claim 10, wherein a buffer chamber is interposed between the sensing chamber and the flow chamber, and the buffer chamber communicates with the flow chamber through a filter in low porous material.

12. The regulator according to claim 10, wherein the sensing electrochemical cell and the selective device are separate elements.

13. The sensing device according to claim 9, wherein the sensing electrochemical cell and the selective device are separate elements.

* * * * *